(12) United States Patent
Gosztolya et al.

(10) Patent No.: US 12,161,481 B2
(45) Date of Patent: Dec. 10, 2024

(54) AUTOMATIC DETECTION OF NEUROCOGNITIVE IMPAIRMENT BASED ON A SPEECH SAMPLE

(71) Applicant: Szegedi Tudományegyetem, Szeged (HU)

(72) Inventors: Gábor Gosztolya, Szeged (HU); Ildikó Hoffmann, Szeged (HU); János Kálmán, Szeged (HU); Magdolna Pákáski, Szeged (HU); László Tóth, Szeged (HU); Veronika Vincze, Szeged (HU)

(73) Assignee: Szededi Tudomanyegyetem (HU)

( * ) Notice: Subject to any disclaimer, the term of this patent is extended or adjusted under 35 U.S.C. 154(b) by 576 days.

(21) Appl. No.: 17/415,418

(22) PCT Filed: Dec. 16, 2019

(86) PCT No.: PCT/HU2019/000043
§ 371 (c)(1),
(2) Date: Jun. 17, 2021

(87) PCT Pub. No.: WO2020/128542
PCT Pub. Date: Jun. 25, 2020

(65) Prior Publication Data
US 2022/0039741 A1  Feb. 10, 2022

(30) Foreign Application Priority Data

Dec. 18, 2018 (HU) .................................. P1800432
May 17, 2019 (HU) .................................. P1900166

(51) Int. Cl.
*A61B 5/00* (2006.01)
*G10L 15/02* (2006.01)
(Continued)

(52) U.S. Cl.
CPC .......... *A61B 5/4803* (2013.01); *A61B 5/4088* (2013.01); *A61B 5/7267* (2013.01);
(Continued)

(58) Field of Classification Search
CPC ... A61B 5/4803; A61B 5/4088; A61B 5/7267; G10L 15/04; G10L 25/66; G10L 2015/025; G10L 25/87; G16H 50/20
(Continued)

(56) References Cited

U.S. PATENT DOCUMENTS 6,873,953 B1 * 3/2005 Lennig .................... G10L 25/87
704/E11.005
7,133,535 B2 * 11/2006 Huang .................. G06V 40/20
704/E21.02
(Continued)

OTHER PUBLICATIONS

"Igras-Cybulska, Magdalena & Ziolko, B. & Żelasko, Piotr & Witkowski, Marcin. (2016). Structure of pauses in speech in the context of speaker verification and classification of speech type. EURASIP Journal on Audio Speech and Music Processing. 18. 18. 10.1186/s13636-016-0096-7." (Year: 2016).*
(Continued)

*Primary Examiner* — Thuykhanh Le
(74) *Attorney, Agent, or Firm* — Wood Herron & Evans LLP (57) ABSTRACT

The invention is a method for automatic detection of neurocognitive impairment, comprising,
generating, in a segmentation and labelling step (11), a labelled segment series (26) from a speech sample (22) using a speech recognition unit (24); and
generating from the labelled segment series (26), in an acoustic parameter calculation step (12), acoustic parameters (30) characterizing the speech sample (22).
(Continued)

The method is characterised by
  determining, in a probability analysis step (14), in a particular temporal division of the speech sample (22), respective probability values (38) corresponding to silent pauses, filled pauses and any types of pauses for respective temporal intervals thereof;
  calculating, in an additional parameter calculating step (15), a histogram by generating an additional histogram data set (42) from the determined probability values (38) by dividing a probability domain into subdomains and aggregating durations of the temporal intervals corresponding to the probability values falling into the respective subdomains; and
  generating, in an evaluation step (13), decision information (34) by feeding the acoustic parameters (30) and the additional histogram data set (42) into an evaluation unit (32), the evaluation unit (32) using a machine learning algorithm.

The invention is furthermore data processing system, a computer program product and a computer-readable storage medium for carrying out the method.

18 Claims, 7 Drawing Sheets

(51) Int. Cl.
  *G10L 15/04*    (2013.01)
  *G10L 25/66*    (2013.01)
(52) U.S. Cl.
  CPC .............. *G10L 15/04* (2013.01); *G10L 25/66* (2013.01); *G10L 2015/025* (2013.01)
(58) Field of Classification Search
  USPC ........................................................ 704/200
  See application file for complete search history.

(56) References Cited

U.S. PATENT DOCUMENTS

| | | | | |
|---|---|---|---|---|
| 11,894,139 | B1* | 2/2024 | Van Hooser | G16H 50/70 |
| 2003/0023435 | A1* | 1/2003 | Josephson | G10L 15/26 |
| | | | | 704/E15.044 |
| 2008/0097754 | A1* | 4/2008 | Goto | G10L 15/26 |
| | | | | 704/214 |
| 2014/0039895 | A1* | 2/2014 | Aravamudan | G06F 16/683 |
| | | | | 704/257 |
| 2014/0201126 | A1* | 7/2014 | Zadeh | A61B 5/165 |
| | | | | 706/52 |
| 2014/0255887 | A1* | 9/2014 | Xu | A61B 5/168 |
| | | | | 434/169 |
| 2015/0058013 | A1* | 2/2015 | Pakhomov | G10L 25/87 |
| | | | | 704/243 |
| 2016/0027278 | A1* | 1/2016 | McIntosh | G08B 21/0423 |
| | | | | 715/741 |
| 2017/0182284 | A1* | 6/2017 | Ueya | A61M 21/02 |
| 2017/0295437 | A1* | 10/2017 | Bertelsen | H04R 25/405 |
| 2017/0365277 | A1* | 12/2017 | Park | G10L 15/1815 |
| 2018/0153477 | A1* | 6/2018 | Nagale | A61B 5/021 |
| 2018/0322894 | A1* | 11/2018 | Kim | G16H 50/50 |
| 2019/0180871 | A1* | 6/2019 | Doerflinger | G16H 50/20 |
| 2020/0246179 | A1* | 8/2020 | Peyman | A61B 18/20 |
| 2021/0110895 | A1* | 4/2021 | Shriberg | G06F 40/20 |
| 2021/0121125 | A1* | 4/2021 | Tokuno | G16H 50/30 |
| 2021/0169417 | A1* | 6/2021 | Burton | A61B 5/4857 |
| 2021/0233660 | A1* | 7/2021 | Omiya | A61B 5/0022 |
| 2022/0007929 | A1* | 1/2022 | Padula | A61B 3/103 |

OTHER PUBLICATIONS

László Tóth et al., Automatic Detection of Mild Cognitive Impairment from Spontaneous Speech using ASR, Proc. Interspeech 2015, Sep. 6, 2015, pp. 2694-2698, XP055680304. (Year: 2015).*

Laszlo Toth et al, Automatic Detection of Mild Cognitive Impairment from Spontaneous Speech using ASR, Proc. Interspeech 2015, Sep. 6, 2015, XP055680304.

Laszlo Toth et al, A Speech Recognition-based Solution for the Automatic Detection of Mild Cognitive Impairment from Spontaneous Speech, Current Alzheimer Research, vol. 15, No. 2, Jan. 3, 2018, XP055680308.

European Patent Office, International Search Report in PCT Application No. PCT/HU2019/000043, Apr. 16, 2020 (4 pgs.).

European Patent Office, Written Opinion of the Internatonal Searching Authority, in PCT Application No. PCT/HU2019/000043 (6 pgs.).

* cited by examiner

AUTOMATIC DETECTION OF NEUROCOGNITIVE IMPAIRMENT BASED ON A SPEECH SAMPLE

This application claims priority, under Section 371, and/or as a continuation under Section 120, to PCT Application No. PCT/HU2019/000043, filed on Dec. 18, 2019, which claims priority to Hungarian Application No. P1900166, filed on May 17, 2019, and Hungarian Application No. P1800432, filed on Dec. 18, 2018.

TECHNICAL FIELD

The present invention is related to the early detection of human cognitive decline of various origins. In this description, any types of cognitive impairment accompanying cognitive decline, including the so-called mild cognitive impairment (MCI), are referred to as "neurocognitive impairment".

The subject of the invention is primarily a method related to the automatic detection of neurocognitive impairment based on a speech sample, without any medical intervention, as well as a data processing system, a computer program product and computer-readable storage medium that are adapted for carrying out the method.

BACKGROUND ART

Increased longevity is a current social phenomenon. However, the process of dementing (mental deterioration) can begin as early as about the age of forty, accompanied by mild cognitive impairment (MCI) that collectively refers to Alzheimer's disease, vascular dementias and other neurodegenerative metabolic, toxic and traumatic forms of dementia, including the early stages thereof. The recognition of MCI is one of the most difficult tasks of clinical medicine (i.e. of a general practitioner, psychiatrist, neurologist, or gerontologist). International practice includes test methods aimed at early recognition and diagnosis, but their effectiveness is not uniform and often the test results themselves do not exhibit any similarity. In addition to that, such test methods are either overly time-consuming, or do not provide an accurate picture of pre-clinical states.

For example, the generally applied test methods include—the following list is not exhaustive—the "Mini Mental Test" (MMSE: Mini-Mental State Examination), a quick test taking only about 15 minutes that is primarily applied for identifying various dementias and for assessing their stage of progress (for details, see for example the articles by M. F. Folstein, S. E. Folstein, P. R. McHugh "Mini-mental state, A practical method for grading the cognitive state of patients for the clinician", J. Psychiatr. Res. 12; 189-198. (1975), and Janka et al. "Dementia szűrővizsgálat cognitív gyors teszt segítségével" (Dementia screening utilizing a quick cognitive test), Orvosi Hetilap 129, 2797 (1988)), or the clock drawing test that measures praxis, gnosis, spatial perception, speed and strategy (see for example J. Kálmán et al. "Óra rajzolási teszt: gyors és egyszerű demencia szűrő módszer" (Clock drawing test: a quick and simple method for screening dementia), Psych. Hung 10; 11-18. (1995)), or the ADAS-Cog test that is used as an internationally accepted measurement tool in medical and pharmacological research related to Alzheimer's disease (Alzheimer's Disease Assessment Scale-Cognitive subscale; see for example the article by the authors W. G. Rosen, R. C. Mohs, K. L. Davis entitled "A new rating scale for Alzheimer's disease" Am. J. Psychiatry 141(11) 1356-1364. (1984)). Using various parameters, all the above cited test methods measure the divergence between the cognitive capabilities of a patient who is presumably affected by neurocognitive impairment and the cognitive capabilities of healthy persons. In all of the above mentioned test processes, tasks adapted for measuring linguistic functions are also included (for example, tasks related to verbal fluency, sentence recall or confrontational naming); in these tests the term "linguistic function" is used to refer to various levels of linguistic performance, i.e. the phonetic/phonological, morphological, syntactic, semantic and pragmatic levels.

Common characteristics of the test methods currently in use are that they are complicated, exceedingly time-consuming and labour-intensive, and that they require the involvement of highly experienced professionals, furthermore they cannot be used as screening tests. This poses serious problems for everyday medical practice. Another problem is that an Internet-based version of these tests is not known, so the tests have to be carried out and evaluated manually. Although the disruption of linguistic and memory functions constitute early symptoms, a screening test adapted for measuring the linguistic aspects of neurocognitive impairment (for example, prodromal Alzheimer's) has not yet been developed, with known aphasia tests not being sensitive enough for the purpose (see the article by authors K. Forbes-McKay, A. Venneri entitled "Detecting subtle spontaneous language decline in early Alzheimer's disease with a picture description task", Neurol. Sci. 26: 243-254. (2005)).

Some efforts have already been made for detecting such parameters of spontaneous human speech (so-called biomarkers) that can be used for diagnosing Alzheimer's disease. It has been found that the temporal analysis of spontaneous speech can be of diagnostic value for differentiating patients with mild Alzheimer's disease from the healthy control group (see the article by the authors I. Hoffmann, D. Németh, D. C. Dye, M. Pákáski, T. Irinyi, J. Kálmán entitled "Temporal parameters of spontaneous speech in Alzheimer's disease", International Journal of Speech-Language Pathology 12/1. 29-34. (2010)).

Efforts have also been made at automating, to a certain extent, the temporal analysis that forms the basis of the diagnosis and can only be carried out manually, and is a very time-consuming and complex task, and so is unsuitable as a tool in everyday medical practice (see the study by the authors L. Tóth, G. Gosztolya, V. Vincze, I. Hoffmann, G. Szatlóczki, E. Biró, F. Zsura, M. Pákáski, J. Kálmán entitled "Automatic Detection of Mild Cognitive Impairment from Spontaneous Speech using ASR", Proc. Interspeech, pp. 2694-2698 (2015)). In this study, speech sounds and phonemes were detected in the speech samples (instead of words), while filled pauses—that often occur in the case of hesitations characteristic of MCI—were identified as special phonemes. According to the findings of the study, automated speech analysis yields only marginally lower-quality results compared to manual evaluation, so the automated machine analysis technique described in the article can be applied for speech analysis aimed at detecting MCI. It is also mentioned in the article that during speech analysis it is not necessary to identify individual phonemes. The disadvantage of this solution is that attention is not paid to a sufficient extent to identifying "hesitation" pauses, i.e. filled pauses, which are thus falsely identified, for example as a speech sound, while filled pauses are of utmost importance for detecting MCI.

The detection of neurocognitive impairment through automated evaluation of speech samples by a machine is also addressed in a study by the authors Laszlo Tóth, Ildiko Hoffmann, Gabor Gosztolya, Veronika Vincze, Greta Szatloczki, Zoltan Banreti, Magdolna Pákáski, Janos Kálmán entitled "*A Speech Recognition-based Solution for the Automatic Detection of Mild Cognitive Impairment from Spontaneous Speech*", Curr. Alzheimer Res. 15:(2) 130-138 (2018). In the course of the method applied in the study, speech samples are segmented by recognizing phonemes, with intra-speech pauses and hesitation pauses filled with some speech sound also being identified, i.e. these filled pauses are considered as special phonemes. During phoneme identification, the accuracy of identification is not examined, and, particularly, the probability of the phoneme identified by the speech recognition system as the most probable one for the given segment is not evaluated. After performing segmentation, acoustic biomarkers are calculated, which acoustic features are then processed by a machine learning algorithm and are evaluated to decide whether the patient suffers from MCI or not. As it is pointed out also in this study, it is not required to accurately identify the particular phonemes during the process for determining the acoustic parameters. The method according to this solution also does not deal with accurately identifying filled pauses, or with the treatment of segments that are falsely identified due to that.

A publication cited in the above mentioned article, by the authors K. López-de-Ipina et al., entitled "On the Selection of Non-Invasive Methods Based on Speech Analysis Oriented to Automatic Alzheimer Disease Diagnosis", Sensors 13, 6730-6745 (2013), also deals with the automated diagnosis of Alzheimer's disease based on speech samples. The authors examined the speech samples by determining characteristics such as the fluency of speech, Higuchi fractal dimension, emotional speech analysis and emotional temperature. According to the article, the features pertaining to the fluency of spontaneous speech also involve the calculation of histograms for the average of the (number of) speech-containing segments and segments not containing speech (i.e. pause segments) of the speech samples, and also for the percentage ratio of speech to pauses. Examples for the diagrams called "histograms" by the authors can be found in an earlier publication by the same authors that is cited in the present article (K. López-de-Ipina et al., "New Approaches for Alzheimer's Disease Diagnosis Based on Automatic Spontaneous Speech Analysis and Emotional Temperature" Ambient Assist. Living Home Care, 7657, 407-414 (2012)). In the above study published by K. López-de-Ipina in 2012, the percentage ratio of speech and pauses and the average length of speech-containing temporal intervals are compared in diagrams (FIGS. 3 and 4) for speech samples with a length of 60 seconds, gathered from eight subjects. It can be concluded that the diagrams in question show bar charts and not histograms, because they show features of speech samples gathered from various independent subjects rather than values corresponding to different values or value ranges of a single given variable. Also, the features indicated in the charts are not utilized for generating automatic decision information; it is only established in a qualitative manner that the speech fluency of subjects suffering from Alzheimer's disease is lower compared to the control group, i.e. Alzheimer's patients pause during speech more often than control group subjects, and the average length of speech-filled temporal intervals is also reduced.

In the above article from 2013, the accuracy of the diagnosis is studied by applying particular feature groups and the combinations thereof. Of the feature groups, the accuracy of the diagnosis was lowest applying features related to the fluency of spontaneous speech, and the accuracy could only be improved by also applying further features. As can be seen also in the bar chart shown in FIG. 6 of the article, illustrating the aggregated error rate of the various types of the features and the decisions made by combining them, the aggregate error rate of classifying the speech samples evaluating only the features related to the fluency of spontaneous speech is almost 180%, the greatest part of which error rate resulting from the false recognition of first-phase, i.e. early stage (ES) Alzheimer's disease. This indicates that the involvement of the bar charts (called histograms by the authors) in the decision algorithm is shown to be markedly disadvantageous in the article.

Automated speech recognition algorithms and software known in the prior art, for example HTK (http://htk.eng.cam.ac.uk/) or PRAAT (http://www.praat.org/) usually apply a probabilistic model, for example, hidden Markov model for recognizing particular phonemes or words of the speech sample, i.e. they determine the word or phoneme that can be heard with the greatest probability during a given temporal segment. With default settings, the output of the algorithms returns the identified words or phonemes without the associated probability values determined during the course of the recognition process, so the use of such probability values for further analysis is not known from the prior art.

In U.S. Pat. No. 5,867,816 an automatic speech recognition system is disclosed that is adapted to divide digitized speech into phonemes and then label the phonemes. Speech processing is carried out in time windows that preferably have a length of 20-25 ms and can also overlap with each other. The overlap is preferably in the order of 5-10 ms. After performing a transformation, for example fast Fourier transformation (FFT) on the time windows, a trained neural network is applied for determining the phonemes in each time window. The invention has the disadvantage that the pauses occurring in spontaneous speech are not taken into account during automated segmentation, but instead they are eliminated.

US 2009/0076817 A1 discloses a speech recognition method for determining the boundaries between subsequent speech sounds, and then gives a probabilistic estimation for the phonemes found in the given interval.

In U.S. Pat. No. 5,333,275 a method for making a time aligned transcription of a sound recording of spontaneous speech is disclosed. The length of the sound recordings is typically 5-10 minutes, with time aligning being made more difficult by the hesitations occurring in spontaneous speech. For providing proper time alignment, extralinguistic features included in the sound recording, for example external noises or features arising from spontaneous speech also have to be addressed by the method. In the method, speech sounds and certain extralinguistic features, namely pauses, the sounds of inhalation and exhalation and the sounds of lip smacking are identified applying separate hidden Markov models; other extralinguistic features, such as pauses of hesitation and filled pauses, are not modelled by the method. The method applies a cumulative histogram for discriminating the utterances of two speakers speaking at the same time.

In U.S. Pat. No. 7,835,909 B2 a speech recognition method is disclosed that applies a backward cumulative histogram for normalizing feature vectors of sounds. The disadvantage of cumulative histograms calculated in a traditional manner, i.e. in an order from smallest to largest value, is that they also strongly accumulate noises. By applying backward cumulative histograms, i.e. histograms calculated in an order from largest to smallest value, noises appear less dominantly in sound recordings made in noisy environments, so they will be similar to recordings taken in silent conditions.

DESCRIPTION OF THE INVENTION

In light of the known solutions the need has arisen for providing a speech analysis method that allows for the early recognition and/or screening of neurocognitive impairment in a simple, effective, fast and objective manner by anyone, i.e. without requiring the intervention of a trained personnel or a physician.

The object of the technical solution according to the invention is to provide an automated speech analysis method adapted for the detection of neurocognitive impairment that eliminates the drawbacks of prior art solutions to the greatest possible extent.

The primary objective of the invention is to provide an automated method that allows for the early recognition of neurocognitive impairment effectively and objectively, with the smallest possible error rate, and permitting quick data processing.

A further objective of the invention is to provide a method that is simple, cheap, can be carried out by anyone irrespective of their training or education, and can be applied for any language after making the necessary adjustments and calibrations.

The objectives of the invention also include the provision of a method that can be applied for the detection of neurocognitive impairment or for determining the severity of neurocognitive impairment also in pharmacological tests, by means of which the effectiveness of medication applied for treating certain types of neurocognitive impairment can be assessed.

The objectives of the invention also include a data processing system, computer program product, and computer-readable storage medium adapted for carrying out the method.

The objectives set before the invention have been fulfilled by providing the method for the automatic detection of neurocognitive impairment according to claim 1, the data processing system according to claim 16, and the computer program product according to claim 18. Preferred embodiments of the invention are defined in the dependent claims.

The advantage of the technical solution according to the invention is that it generates decision information based on a speech sample gathered from a human subject in a completely automated manner, based on which information it can be decided if the subject suffers from neurocognitive impairment. The early recognition or presumption of neurocognitive impairments allows the presumed patient to consult a medical specialist in time.

In the case of machine learning algorithms applied for any type of recognition task, the quality and information content of the training data is generally of high importance. In case a recognition algorithm can be fed with training data that are rich in information, then the resulting recognition process will be effective and accurate. By way of example, with image recognition algorithms a transformed version of the image to be recognized (for example, a version with enhanced edges or suppressed background) can be applied, which improves the accuracy of recognition. Similarly, in the case of speech recognition it is also expedient to apply such aggregated information, derived from the original speech sample, that can improve recognition accuracy when fed into the recognition algorithm. Related to speech recognition the prior art includes references to a number of derived and aggregated parameters that can be fed to a speech recognition algorithm. Yet, the application of such parameters has not resulted in a breakthrough in the field of the invention as far as the improvement of recognition and decision accuracy is concerned.

In a manner summarized in the introduction, in prior art solutions such probability values that characterize particular examined segments/phonemes are not included in the decision/recognition process, and instead the probability values are applied for selecting the phoneme corresponding to the greatest probability value and labelling it as relevant. There is a general consensus in the field according to which the probability values, and more particularly, smaller probability values reflect the uncertainty of recognition, so including them in the decision process will result in more uncertainty and poorer accuracy. Similarly, the generation of such aggregated information pertaining to the speech sample that contains not only a single aggregated parameter but includes additional information related to the entirety of the speech sample, i.e. to all relevant temporal intervals thereof, is also not included in the prior art. Accordingly, in prior art technical solutions such extra information is not even taken into account for decision-making.

Our experiments have led us to the recognition that the histograms generated using probability values calculated for physical parameters of the speech sample, for example for the pauses included therein constitute such novel, aggregated representations of the physical speech sample that contain data allowing for generating more accurate decision information than before, with the advantages provided by the more accurate decision information far exceeding the disadvantages implicated by extra calculations and information loss. Contrary to the teaching provided by the state of the art, and to the general technical consensus in the field, we have also recognized that by applying the histogram calculated according to the invention from the physical parameters (pauses) of the speech sample for generating the decision information an accurate, reliable and quick decision can be made, which makes it unnecessary to determine (by performing extra calculations) and utilize other parameters included in the prior art, such as fractal dimensions, emotional temperatures, etc. A further advantage of the invention is that the method is adapted for being utilized in the course of pharmacological tests, as it is capable of detecting smaller-scale cognitive changes compared to known solutions.

BRIEF DESCRIPTION OF THE DRAWINGS

Preferred embodiments of the invention are described below by way of example with reference to the following drawings, where.

MODES FOR CARRYING OUT THE INVENTION

Figure 1:
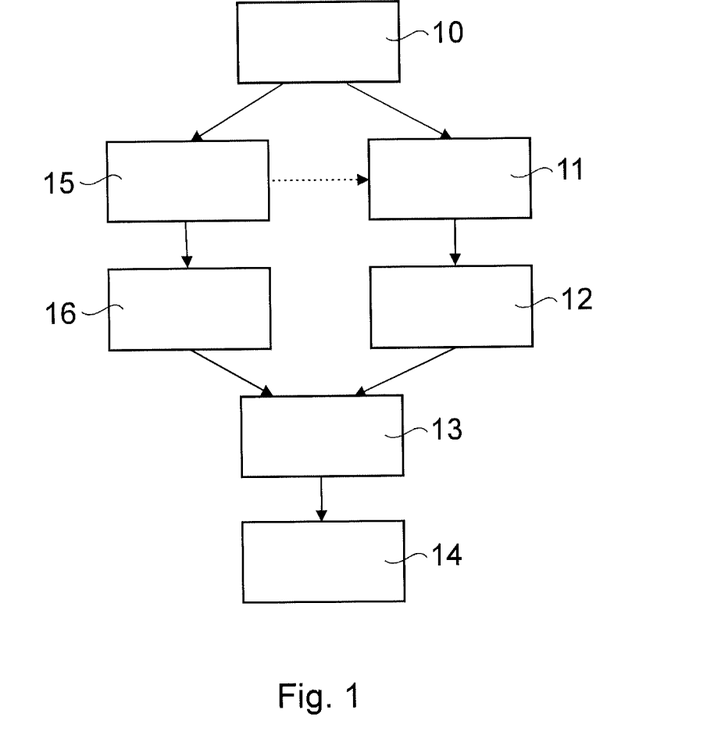
FIG. 1 is a flow diagram of a preferred embodiment of the method according to the invention.

In FIG. 1 there can be seen a flow diagram of a preferred embodiment of the method according to the invention. In the course of the method, in a speech sample generation step 10 a speech sample is generated, preferably by applying a microphone.

In a segmentation and labelling step 11, the speech sample is processed, generating a labelled segment series from the speech sample by using a speech recognition unit. Any type of speech recognition system (even a prior art one) can be preferably applied as a speech recognition unit. The features of the speech recognition unit, as well as the requirements therefor, are described in more detail in relation to FIG. 2.

The labelled segment series includes phoneme labels, silent pause labels, and filled pause labels as different label types, and also contains the initial and final time instances for each label. Preferably, a separate phoneme label is assigned to each phoneme, but the invention also works properly applying such a simplified solution wherein a common phoneme label is applied for all phonemes, i.e. wherein different phonemes are not treated separately, and only the pauses (without a filler, i.e. silent pauses) of speech are taken into account. Silent pauses are temporal intervals of the speech sample wherein no speech can be heard, i.e. they contain silence. Filled pauses are such temporal intervals of the speech sample that are not silent but where speech is also not produced. These pauses, which are typically filled with some speech sound or filler, reflect the hesitation of the speaker/user. For example, filled pauses can be verbal hesitations such as "hmm", "uhm", or the using of other "hesitation sounds" or fillers (in Hungarian, "ööö"-ing, or in the case of English speakers, saying 'um', 'uh', or 'er'). Preferably, the labels are the phoneme labels corresponding to the speech sounds of the language spoken in the given speech sample, complemented with the silent pause and filled pause labels.

In an acoustic parameter calculation step 12, acoustic parameters characteristic of the speech sample are generated from the labelled segment series, which acoustic parameters are, in an evaluation step 13, fed into an evaluation unit that applies a machine learning algorithm for producing decision information. Based on the decision information, it can be decided if the person providing the speech sample is potentially affected by neurocognitive impairment. The evaluation unit adapted for providing the decision information is also described in more detail in relation to FIG. 2.

In the course of processing the speech sample, in a probability analysis step 14, respective probability values are determined corresponding to silent pauses, filled pauses and any types of pauses (i.e. either silent or filled pauses) for respective temporal intervals of a particular temporal division of the speech sample.

The probability values obtained in the probability analysis step 14 are preferably used for generating the labelled segment series in the segmentation and labelling step 11, in the course of which the labels of the labelled segment series are determined based on the highest-probability phonemes (including the silent and filled pauses), the segment boundaries being given by the outer boundaries of adjacent temporal intervals that can be labelled with the same label.

In an additional parameter calculating step 15, the probability values determined in the probability analysis step 14 are used for calculating a histogram by generating an additional histogram data set from the determined probability values through dividing the probability domain into subdomains and aggregating the durations of the temporal intervals corresponding to the probability values falling into the respective subdomains. In the evaluation step 13, decision information is generated by feeding the acoustic parameters and the additional histogram data set into the evaluation unit that applies a machine learning algorithm. The combined evaluation, in the evaluation step 13, of the acoustic parameters derived from the speech sample and the additional histogram data set significantly increases the accuracy of the decision information.

Figure 2:
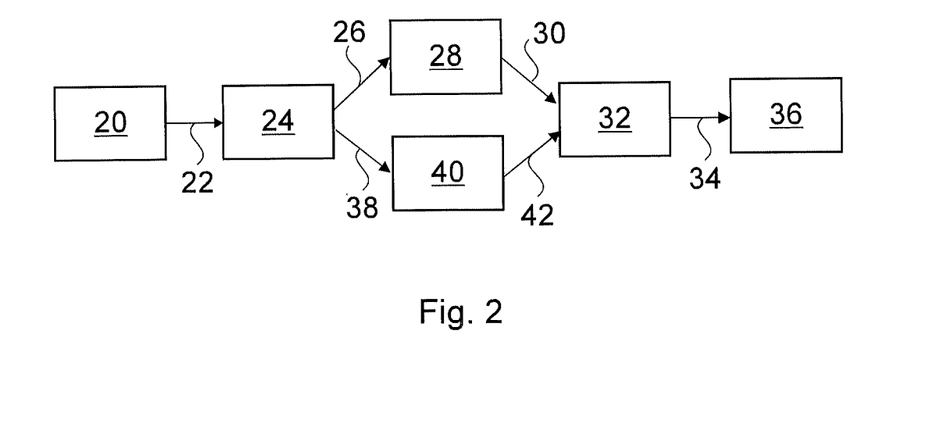
FIG. 2 is the block diagram of a preferred embodiment of the system performing the method according to the invention.

In FIG. 2, a preferred embodiment of the data processing system adapted for carrying out the steps of the method according to the invention is illustrated. For performing the steps of the method, the data processing system comprises a speech recognition unit 24 adapted for generating a labelled segment series 26 from a speech sample 22, and a parameter extraction unit 28 that is connected to the output of the speech recognition unit 24 and is adapted for extracting acoustic parameters 30 from the labelled segment series 26. The data processing system further comprises an additional parameter extraction unit 40 that is connected to the output of the speech recognition unit 24 and is adapted for generating an additional histogram data set 42, and an evaluation unit 32 that is connected to the outputs of the parameter extraction unit 28 and the additional parameter extraction unit 40 and is adapted for performing the evaluation of the acoustic parameters 30 and the additional histogram data set 42.

The data processing system preferably comprises a sound recording unit 20 connected to the input of the speech recognition unit 24, and/or a display unit 36 connected to the output of the evaluation unit 32, and/or a database, the database being interconnected with the sound recording unit 20, with the speech recognition unit 24, with the parameter extraction unit 28, with the additional parameter extraction unit 40, with the evaluation unit 32 and/or with the display unit 36.

In the speech sample generation step 10 of the method (as shown in FIG. 1), a speech sample 22 of human speech is recorded, preferably applying the sound recording unit 20, followed by passing on the recorded speech sample 22 to the speech recognition unit 24 and/or the database (the database is not shown in the figure). The sound recording unit 20 is preferably a telephone or a mobile phone, more preferably a smartphone or a tablet, while the sound recording unit 20 can also be implemented as a microphone or a voice recorder. The sound recording unit 20 is preferably also adapted for conditioning and/or amplifying the speech sample 22.

The recorded speech sample 22 is processed by the speech recognition unit 24, wherein the speech sample 22 is either retrieved from the sound recording unit 20 or from the database. The speech recognition unit 24 can be implemented by applying a speech recognition system that is known from the prior art and includes commercially available hardware, software, or a combination thereof. Speech recognition systems are typically adapted for performing statistical pattern recognition, which involves, in a training phase, the estimation of the distribution of data belonging into various classes, for example, speech sounds by using of a large amount of training data, and, in a testing phase, the classification of a new data point of unknown class, usually based on the so-called Bayes decision rule, i.e. on the highest probability values. A requirement for the speech recognition system applied in the method according to the invention is that it should generate an output consisting of phonemes (as opposed to words), also indicating the start and end point of each phoneme. A labelled segment series 26 that is segmented by applying the initial and final time instances of the phonemes and is labelled to indicate the phoneme included in the given segment of the speech sample 22 is generated by the output of the speech recognition unit 24 (segmentation and labelling step 11). The speech recognition unit 24 is further adapted to apply labels, in addition to the phonemes corresponding to the language of the speech sample 22, also to the silent pauses and the filled pauses. Thus, the labelled segment series 26 also contains segment information related to the silent and filled pauses.

Preferably, the speech recognition system that is known in the field as HTK and is publicly available free of charge (http://htk.eng.cam.ac.uk/) can be applied as the speech recognition unit 24.

The labelled segment series 26 is passed on by the speech recognition unit 24 to the parameter extraction unit 28 and/or to the database.

In addition to the above, in a probability analysis step 14, the speech recognition unit 24 determines, in a particular temporal division of the speech sample 22, respective probability values 38 corresponding to silent pauses, filled pauses and all types of pauses for pre-defined temporal intervals of the sample. For determining the probability values 38, the speech sample 22 is divided by the speech recognition unit 24 in a predetermined manner into temporal intervals, preferably temporal intervals of identical length, more preferably, overlapping temporal intervals. In a particularly preferable realization, the speech sample 22 is divided by the speech recognition unit 24 into temporal intervals having a length of 10-50 ms and an overlap of 20-50%. For example, temporal intervals having a length of 25 ms and an overlap of 10 ms are applied.

Figure 3:
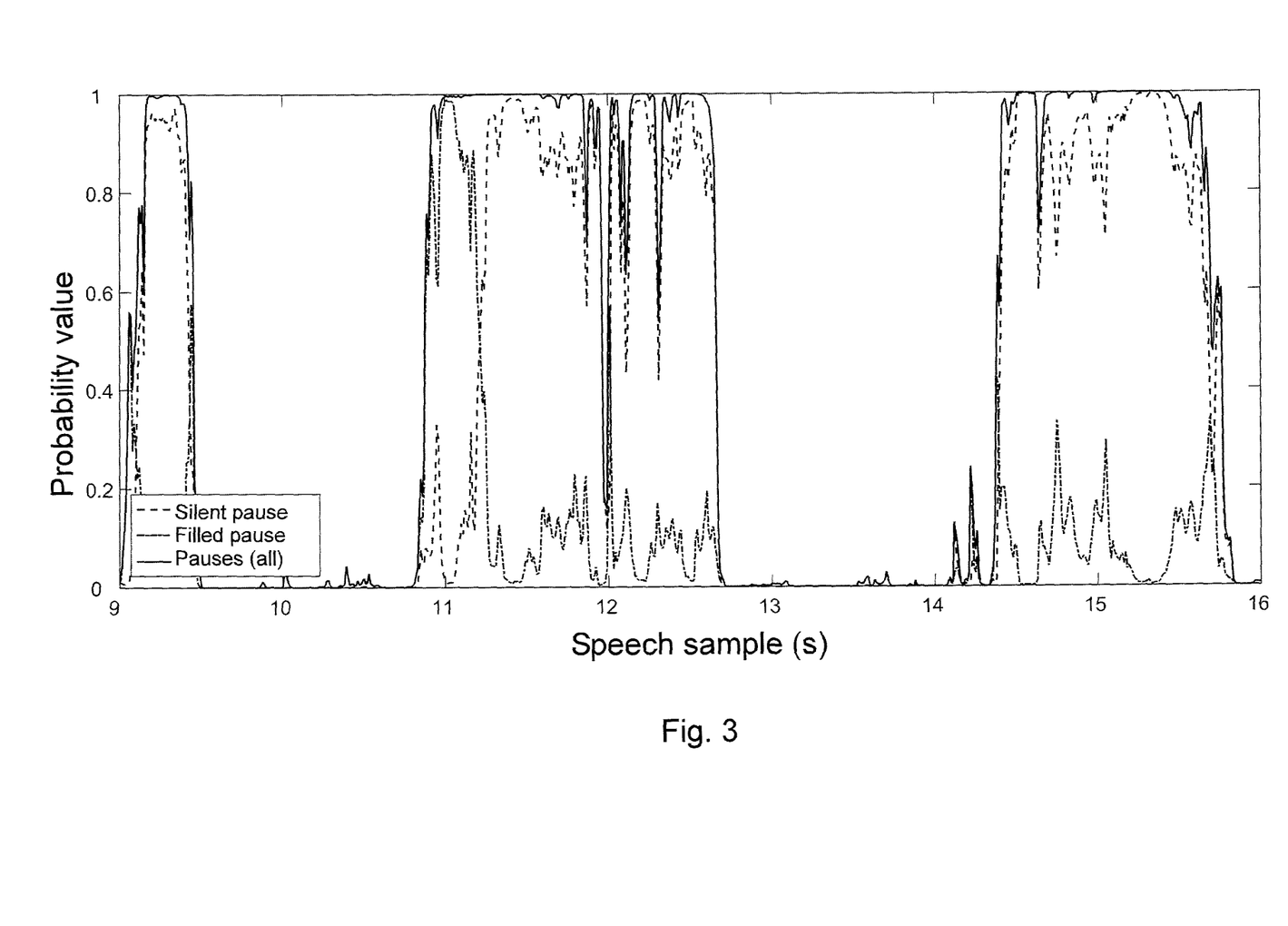
FIG. 3 is a diagram showing the probabilities estimated for silent pauses, filled pauses and for any pauses combined, over a given temporal interval of a speech sample.

For each temporal interval, the probability values of all the phonemes, and also of silent and filled pauses, are determined by the acoustic model of the speech recognition unit 24. FIG. 3 shows, as a function of time, the respective probability values 38 determined for a particular temporal interval of the speech sample 22 for silent pauses, filled pauses and aggregately for any types of pauses.

In a preferred embodiment, the probability values 38 obtained in the probability analysis step 14 are used for determining labels and segment boundaries in the segmentation and labelling step 11 (indicated with a dashed arrow in FIG. 1). In this case, the highest-probability phonemes (complemented by the silent and filled pauses) corresponding to each temporal interval will become the labels included in the labelled segment series 26, while the segment boundaries can be determined from the boundaries of the temporal intervals. In another preferred embodiment, the labels and segment boundaries of the labelled segment series 26 can also be obtained applying an alternative, known method.

The parameter extraction unit 28 generates acoustic parameters 30 characteristic of the speech sample 22 from the labelled segment series 26, which labelled segment series 26 is received from the speech recognition unit 24 or retrieved from the database. The generated acoustic parameters 30 are passed on by the parameter extraction unit 28 to the database or to the evaluation unit 32.

A characteristic feature of the acoustic parameters 30 extracted by the parameter extraction unit 28 is that they can be computed from the length of the particular segments of the labelled segment series 26, wherein a value of at least one of the acoustic parameters 30 being significantly different in the case of healthy subjects and patients presumably exhibiting neurocognitive impairment. The acoustic parameters 30 therefore contain information applicable for distinguishing healthy subjects from patients presumably exhibiting neurocognitive impairment. A comparison of acoustic parameters 30 extracted from speech samples 22 from patients exhibiting neurocognitive impairment and from speech samples from a control group was performed via a statistical method. A two-sample statistical t-test was preferably applied as a statistical method. The significance values of the two-sample statistical t-test calculated for the acoustic parameters 30 of patients exhibiting neurocognitive impairment and of the control group are summarized in Table 1. The definitions of the acoustic parameters 30 included in Table 1 are summarized in Table 2. In Table 1, the acoustic parameters 30 for which the significance values are lower than 0.05, i.e. in case of which a significant difference can be detected between patients exhibiting neurocognitive impairment and the control group are shown in bold type.

TABLE 1

Acoustic parameters 30 and associated significance levels

| Acoustic parameter | significance value |
|---|---|
| total duration of speech sample (ms) | 0.0005 |
| speech rate (1/s) | 0.1346 |
| articulation rate (1/s) | 0.1073 |
| number of silent pauses | 0.0018 |
| number of filled pauses | 0.0011 |
| number of all pauses | 0.0008 |
| total length of silent pauses (ms) | 0.0037 |
| total length of filled pauses (ms) | 0.0011 |
| total length of all pauses | 0.0014 |
| silent pauses/duration of speech sample (%) | 0.3850 |
| filled pauses/duration of speech sample (%) | 0.0398 |
| all pauses/duration of speech sample (%) | 0.2294 |
| number of silent pauses/duration of speech sample (%) | 0.1607 |
| number of filled pauses/duration of speech sample (%) | 0.1160 |
| number of all pauses/duration of speech sample (%) | 0.3861 |
| average length of silent pauses (ms) | 0.1247 |
| average length of filled pauses (ms) | 0.1308 |
| average length of all pauses (ms) | 0.0913 |

TABLE 2

Definition of acoustic parameters 30

| Parameter | Definition |
|---|---|
| articulation rate | number of articulated speech sounds per second during the sample excluding the duration of pauses (1/s) |
| speech rate | number of speech sounds per second during the sample including the duration of pauses (1/s) |

TABLE 2-continued

Definition of acoustic parameters 30

| Parameter | Definition |
|---|---|
| number of pauses | number of all pauses during the total duration of the speech sample |
| duration of pauses | combined duration of all pauses during the speech sample (ms) |
| pauses/full duration of speech sample | combined duration of all pauses/ total duration of speech sample (%) |
| pause ratio | the ratio of the number of all pauses to the number of all segments detected over the total duration of the speech sample (%) |
| average length of pauses | average length of pauses calculated for all pauses (ms) |

As it can be discerned from Table 1, the number of silent pauses, filled pauses, and the aggregate number of pauses (any pauses), as well as the combined duration of the pauses shows a significant difference between the group with neurocognitive impairment and the control group. Another acoustic parameter 30 that also shows significant difference is the ratio of the length of filled pauses to the total duration of the speech sample 22, so a further examination of filled pauses seems particularly preferable. Because filled pauses can be easily confused with certain speech sounds—in Hungarian, particularly the sounds 'ö' /ø/, /ø:/, 'm' and 'n', and in English, particularly the sounds 'ah' or 'uh' /ʌ/, 'er' /ɜː/ and 'um' /ʌm/—it is also preferable to specify certain parameters similar to the parameters of filled pauses also for these phonemes (i.e. number of occurrences, combined length and average length of occurrences, the deviation of lengths), and add these to the existing set of acoustic parameters 30.

In the additional parameter calculating step 15 according to the invention, additional parameters characteristic of the speech sample 22 are calculated, in the course of which calculation an additional histogram data set 42 is generated from the probability values 38. In the preferred embodiment according to FIG. 2, the additional histogram data set 42 is generated by the additional parameter extraction unit 40. The additional parameter extraction unit 40 is preferably a device having a computational capacity, for example a computer, a tablet computer, or a mobile phone. In a preferred embodiment, the additional parameter extraction unit 40 and the parameter extraction unit 28 can be implemented in a single device, wherein the computational operations of the acoustic parameter calculation step 12 and the step of calculating additional parameters 15 are executed sequentially or in parallel. The steps of generating the additional histogram data set 42 are described in detail in relation to FIGS. 3-6.

The acoustic parameters 30 and the additional histogram data set 42 utilized for generating decision information 34 are retrieved by the evaluation unit 32 either from the database or from the parameter extraction unit 28 and the additional parameter extraction unit 40. Based on the decision information 34 it can be decided whether the person producing the speech sample 22 under examination is healthy or presumably suffers from neurocognitive impairment. The decision information 34 preferably also contains a decision limit and the corresponding error margins, which allows for more sophisticated decision-making. The decision information 34 is preferably displayed by a display unit 36 that is preferably implemented as a device having a screen, i.e. a smartphone or tablet.

The evaluation unit 32 used for generating the decision information 34 preferably applies a trained machine learning algorithm, and more preferably applies a "Naive Bayes" (NB), linear "Support Vector Machine" (SVM) or "Random Forest"-type machine learning algorithm. Due to the low number of speech samples 22 gathered from known patients with neurocognitive impairment, preferably such a machine learning algorithm can be used in the training phase of the evaluation unit 32 that can be reliably applied even with a small amount (typically, fewer than 100 samples) of training data. For such a small amount of training data, it is preferable to apply the SVM and RF algorithms as a machine learning algorithm. The machine learning algorithms have to be trained using speech samples 22 from patients exhibiting neurocognitive impairment and from a healthy control group. The effectiveness of machine learning algorithms can usually be increased when training data having a multitude of well chosen characteristics is available. We have recognised that the additional histogram data set 42 is capable of describing the speech sample 22 in such a manner that increases the accuracy and effectiveness of the decisions made by the machine learning algorithm applied in the evaluation unit 32. The speech sample 22 is described by the additional histogram data set 42 with parameters that are independent of the length of the speech sample 22 and are defined based on probability values. This is a different approach with respect to the earlier one applying the acoustic parameters 30, and yields additional training information in relation to the pauses contained in the speech sample 22. By training the machine learning algorithm applying both the acoustic parameters 30 and the additional histogram data set 42, the machine learning algorithm operates more effectively and makes higher-quality decisions.

After training the machine learning algorithm, the evaluation unit 32 uses the trained algorithm for generating the decision information 34. To increase the reliability of the method, the machine learning algorithm can be trained further from time to time applying the new data that are stored in the database in the course of the method.

By generating the decision information 34, the evaluation unit 32 determines whether the acoustic parameters 30 of the speech sample 22 under examination and the additional histogram data set 42 are closer to the corresponding parameters of the speech sample 22 of the group with neurocognitive impairment, or those of the speech sample 22 corresponding to the control group. The trained machine learning algorithm applied by the evaluation unit 32 preferably assigns a respective probability value (a value between 0 and 1) to the events of the subject belonging to one or the other possible decision group; the sum of the probability values is 1. The trained machine learning algorithm of the evaluation unit 32 preferably also determines the decision limits (together with their error limits) corresponding to the decision information 34, so the decision information 34 preferably also contains the decision limits thus determined and the error limits thereof. The decision limit is a probability limit above which the subject producing the speech sample 22 will be considered to belong to a specific group, for example the group of subjects with neurocognitive impairment, while under the limit the subject is considered to belong to the other group, for example the group of healthy subjects. In the following, the term "decision limit" is taken to mean the decision limit determined for the group with neurocognitive impairment, i.e. with a decision limit of 0.5, in case the trained machine learning algorithm of the evaluation unit 32 determines a probability value that is lower than 0.5 for belonging to the group with neurocognitive impairment, then the subject producing the given speech sample 22 will be classified as part of the control group, i.e. will be classified as healthy. If this probability value is 0.5 or higher, then the subject will be classified as part of the group having neurocognitive impairment.

If the trained machine learning algorithm is biased towards one of the groups, for example the training data applied for training the algorithm includes a higher number of samples belonging to one group, then the decision limit can be preferably set higher or lower than 0.5, depending on the direction of the bias of the trained machine learning algorithm. For example, if there is a bias towards the control group (the training data contain a higher number of samples from the control group), the decision limit is preferably set to a value that is lower than 0.5, while in another example, wherein the training data contain a higher number of samples from the group with neurocognitive impairment, the decision limit preferably should be set to a value that is higher than 0.5.

Other considerations can also be preferably taken into account for determining the decision limit, for example the probability of false decisions, i.e. the sensitivity and specificity of the decision. If false positives are to be avoided, i.e. our aim is to avoid that the speech sample 22 of a healthy subject is classified as part of the group of subjects with neurocognitive impairment, then the decision limit is expediently set higher than 0.5, for example, preferably to a value of 0.6. If, on the contrary, our aim is to identify as many subjects suffering from neurocognitive impairment as possible, even at the cost of falsely classifying some healthy subjects as unhealthy, then it is expedient to set the decision limit to a value lower than 0.5, for example, preferably to a value of 0.4.

The decision limit is preferably determined based on the expected sensitivity and specificity of the decision, preferably applying a separate set of test data that are different from the training data of the machine learning algorithm.

In FIGS. 3-6, an example related to a preferred implementation of the additional parameter calculating step 15 is presented. In the example, the speech sample 22 was divided into temporal intervals having a length of 25 ms, overlapping with each other over a duration of 10 ms, followed by determining, in the probability analysis step 14, the respective probability values 38 of silent pauses, filled pauses and all pauses for each temporal interval. These probability values 38 are shown in FIG. 3 for a temporal interval of the examined speech sample 22, in particular, the interval located between 9 and 16 seconds from the start of the speech sample 22. The probability of all pauses (any pauses) is obtained as the sum of the probability of a silent pause and the probability of a filled pause.

Figure 4:
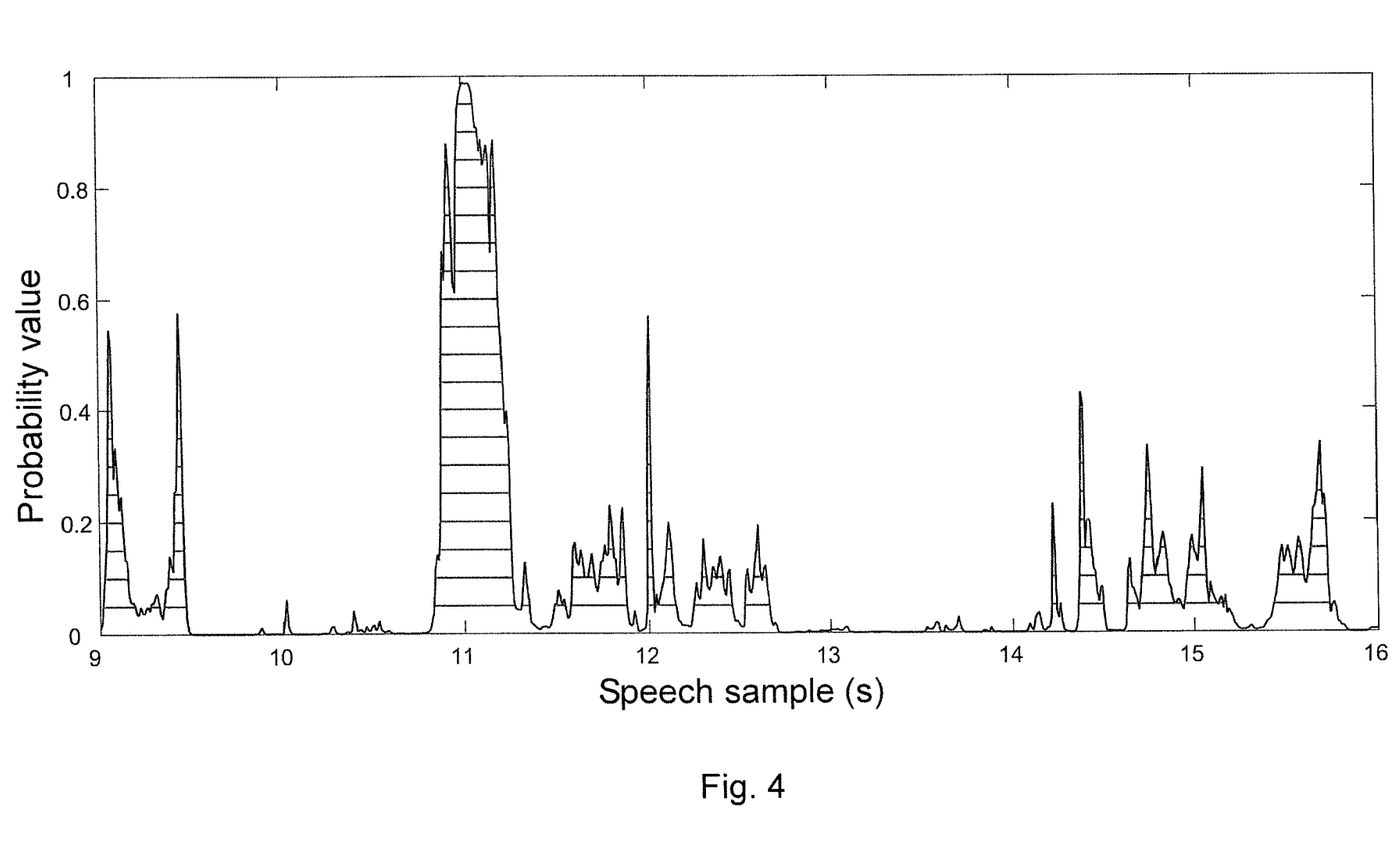
FIG. 4 shows the estimated probability values for filled pauses of the speech sample according to FIG. 3, showing probability limit values as horizontal lines.

FIG. 4 shows the probability values relating to filled pauses as included in FIG. 3. In the figure, the probability domain is divided uniformly into twenty subdomains, so domain boundaries follow each other with a step size of 0.05. The values corresponding to the boundaries of probability domains are indicated in the figure by horizontal lines at the locations where the probability curve surpasses the values corresponding to the probability domain boundaries.

Figure 5:
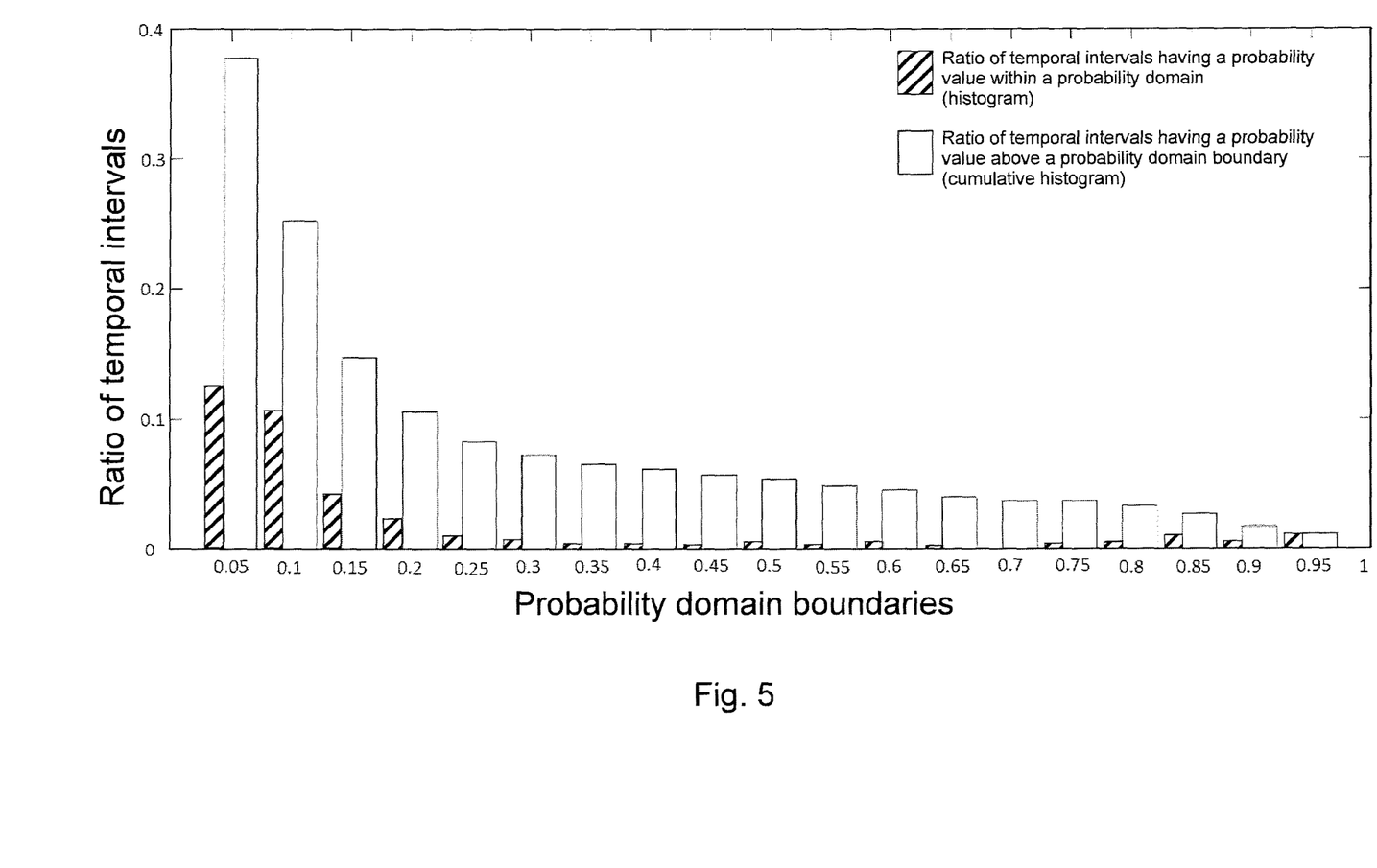
FIG. 5 shows a histogram and a cumulative histogram calculated from the values of FIG. 4.

In FIG. 5, two examples for an additional histogram data set 42 calculated from FIG. 4 are presented. In the first example, the additional histogram data set 42 is generated from the temporal intervals falling between the probability domain boundaries shown in FIG. 4, preferably, the additional histogram data set 42 gives the ratio of temporal intervals having a probability between adjacent probability domain boundaries to the total duration of the speech sample 22, i.e. in the additional parameter calculating step 15 a histogram is generated from the probability values 38 relating to filled pauses. By way of example, the value of the additional histogram data set 42 corresponding to the probability domain boundary value of 0.4 gives the ratio of those temporal intervals to the total duration of the speech sample 22 during which temporal intervals the probability values 38 relating to filled pauses are higher or equal to 0.4 but do not reach the next probability domain boundary value of 0.45.

In a second example, the additional histogram data set 15 is generated from temporal intervals having a probability that is higher than the probability domain boundary values shown in FIG. 4, preferably, the additional histogram data set 42 gives the ratio of temporal intervals having a probability higher than the corresponding probability domain boundaries to the full length of the speech sample 22, i.e. in the step of calculating additional parameters 15 a cumulative histogram is generated from the probability values 38 relating to filled pauses. By way of example, the value of the additional histogram data set 42 corresponding to the probability domain boundary value of 0.4 gives the ratio of those temporal intervals to the total duration of the speech sample 22 during which temporal intervals the probability values 38 relating to filled pauses are higher or equal to 0.4. The cumulative histogram according to the second example can also be generated from the data series of the histogram calculated according to the first example, by determining the aggregate values of the quantities falling into the classes of the histogram corresponding to the respective probability domain boundaries for each class that is greater than the given class.

The additional histogram data set 42 can also be generated such that (not shown in FIG. 5) it is calculated from temporal intervals with a probability that is lower than the probability domain boundaries shown in FIG. 4, i.e. preferably the additional histogram data set 42 gives the ratio of temporal intervals having a probability lower than the corresponding probability domain boundaries to the full length of the speech sample 22. A cumulative histogram is also calculated in this case, however, the aggregation is performed in an order from smallest to largest probability values, i.e. an aggregate value is determined of quantities falling into the classes of the histogram of the first example for all classes that are not greater than the given class.

As with the acoustic parameters 30, the additional histogram data set 42 is characteristic of the speech sample 22 and of the subject giving the speech sample 22 as far as the presence of neurocognitive impairment is concerned. Significance values are determined for each element of the additional histogram data set 42. The significance values can be determined also by applying an arbitrary statistical method, preferably a two-sample statistical t-test. The additional histogram data set 42, however, usually contains a larger number of data than the acoustic parameters 30, for example, if twenty probability domains are applied, the additional histogram data set 42 has 57 elements, and with fifty probability domains it has 147 elements, because, in addition to the filled pauses, the histogram and/or cumulative histogram shown in FIG. 5 has to be generated also for silent pauses, and, aggregately, for any pauses.

The significance values calculated by a two-sample statistical t-test from the elements of the additional histogram data set 42 generated calculating a cumulative histogram are preferably visualized in a non-tabulated format, i.e. in a diagram/graph chart.

Figure 6:
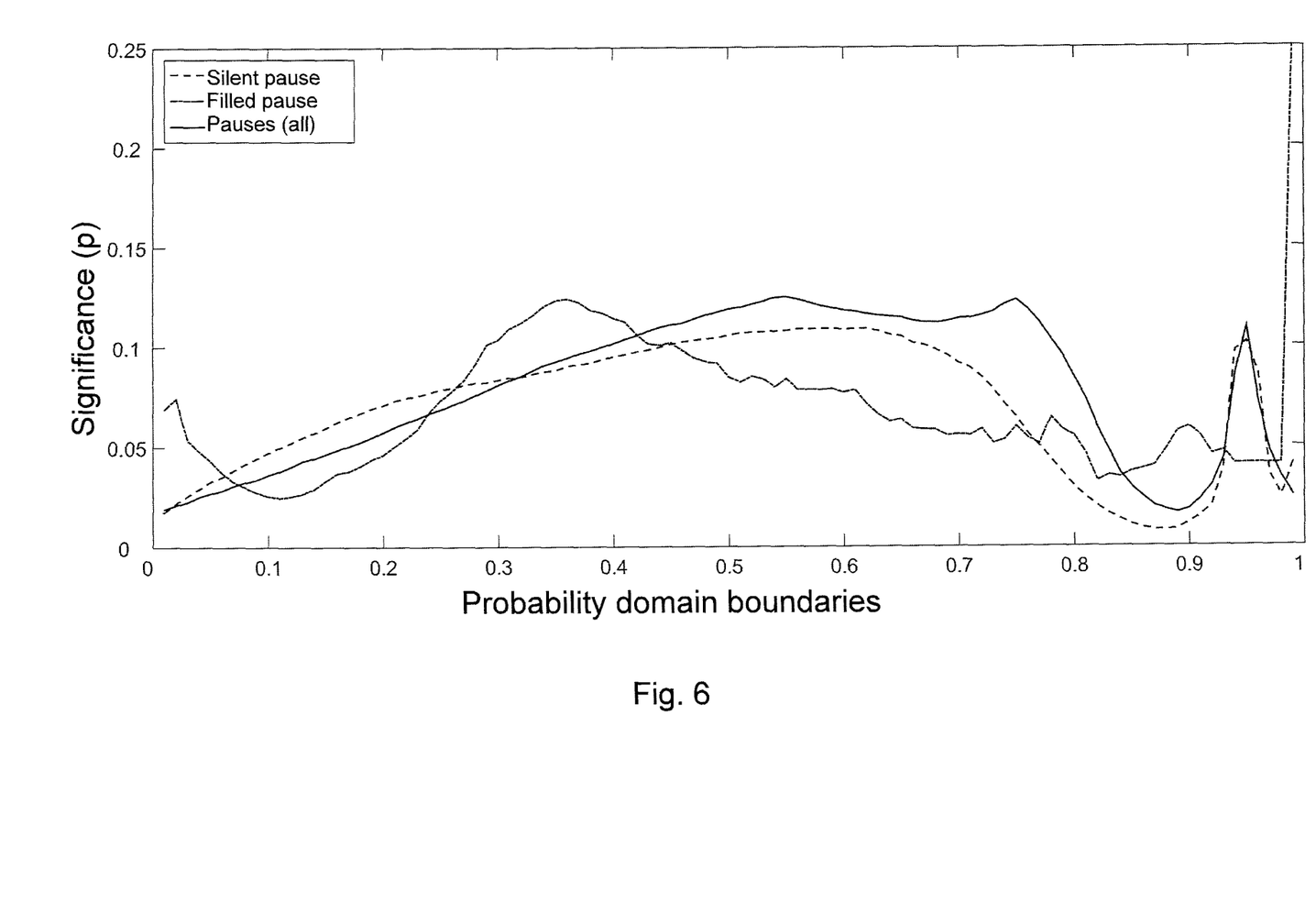
FIG. 6 shows, as a function of the probability limits indicated in FIG. 4, the significance values calculated for the probability values of FIG. 3 from the histograms according to FIG. 5.

In FIG. 6, the significance values corresponding to an additional histogram data set 42 generated by calculating a cumulative histogram are shown as a function of the probability domain boundaries, showing the values corresponding to different types of pause in separate respective curves. The additional histogram data set 42 was generated for the filled pauses, silent pauses and any pauses of the speech sample 22 illustrated in FIG. 3 by calculating a cumulative histogram calculated with twenty probability domains.

In FIG. 6 there can be seen that in the case of silent pauses (dashed-line curve) the features falling between probability domain boundaries of approximately 0.75 and 0.95 show a significant deviation ($p<0.05$) between the speech samples 22 of the control group and patients with neurocognitive impairment. The reason for that is the silent pauses can be easily identified by the speech recognition unit 24, so the probability values 38 corresponding to real silent pauses are high, often exceeding the probability value limit of 0.8.

On the contrary, in the case of filled pauses (dotted-line curve) a significant deviation ($p<0.05$) between the speech samples 22 of the control group and the patients with neurocognitive impairment is obtained at most up to a probability domain boundary of 0.15. This is because it is much harder to identify filled pauses, as they can be easily confused with the phonemes representing hesitation (for example, 'ö', 'm' and 'n'). Because of that, a relatively high probability value 38 that is still lower than 0.5 is often obtained for filled pauses. In such cases there is a danger that filled pauses are not labelled appropriately as filled pauses in the labelled segment series 26, but the given temporal intervals are instead labelled with a phoneme corresponding to a speech sound, and thus the features corresponding to filled pauses will be determined incorrectly during the calculation of acoustic parameters 30. In contrast to that, these filled pauses appear in the additional histogram data set 42.

The method according to the invention can be preferably applied also in pharmacological tests, because it is adapted to detect the occurrence of neurocognitive impairments in a more sensitive manner compared to known solutions, and therefore it can also be applied for measuring the patient's progress and the efficacy of therapy.

Figure 7:
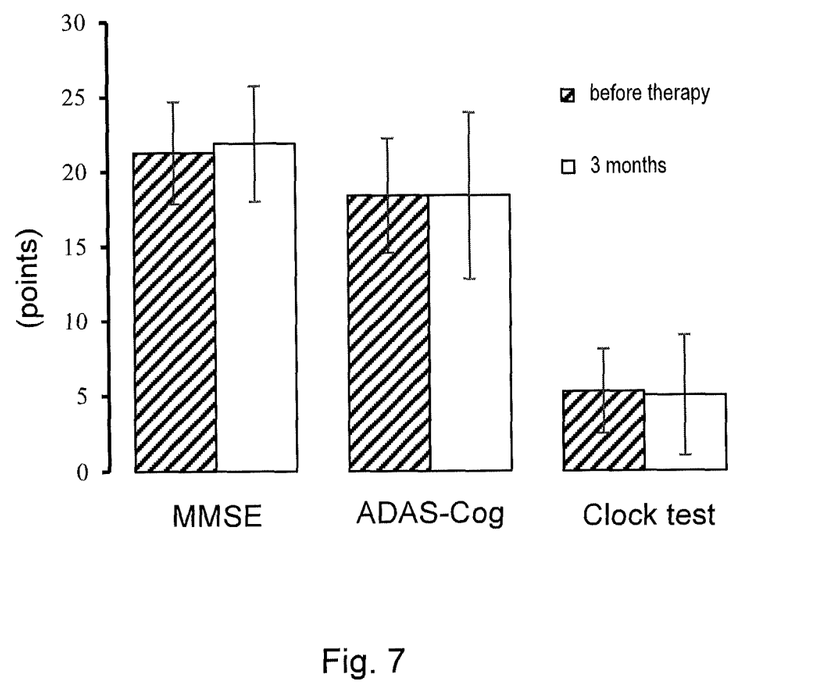
FIG. 7 shows the results of MMSE, ADAS-Cog and clock drawing tests in pharmacological tests related to the therapy of Alzheimer's disease.
Figure 8A:
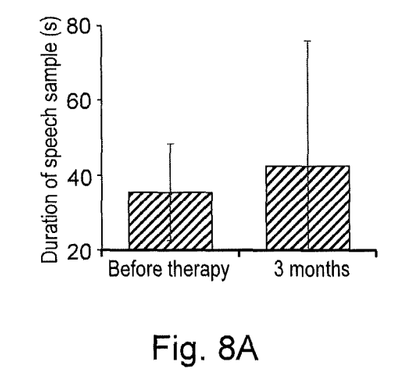
FIGS. 8A-8F show the results of tests (indicating the values of certain acoustic parameters) related to the therapy of FIG. 7 that were carried out by applying the method according to the invention.
Figure 8B:
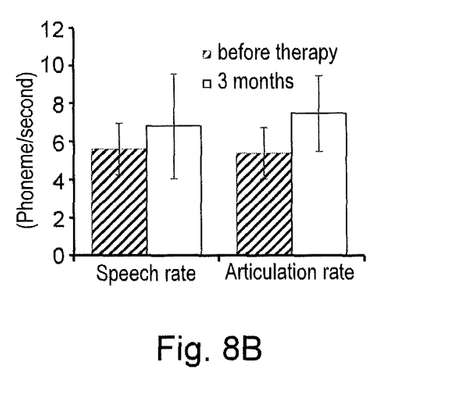
Figure 8C:
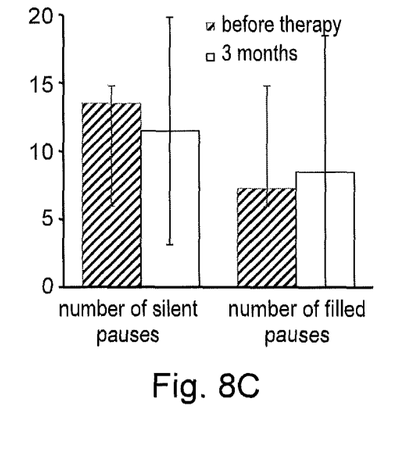
Figure 8D:
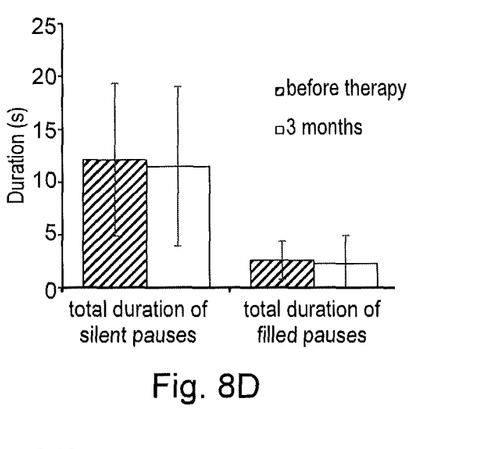
Figure 8E:
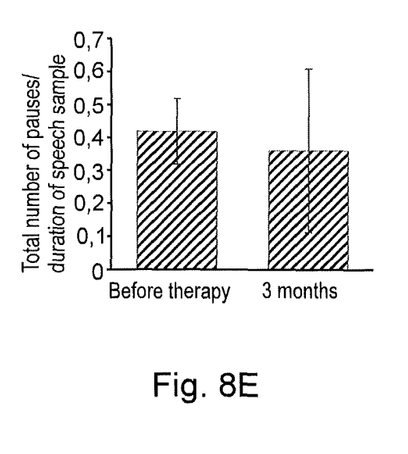
Figure 8F:
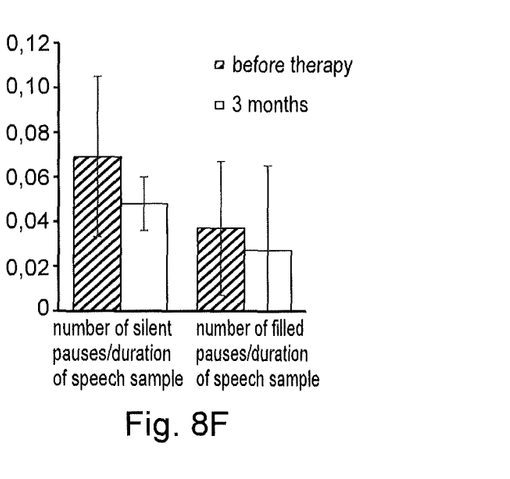

In the following, an exemplary application of the method according to the invention for monitoring the therapy of Alzheimer's disease is described. The currently feasible aim of the therapy of Alzheimer's is to slow the progress of the disease. One of the most frequently applied commercially available drugs is donepezil, an acetylcholinesterase inhibitor. Therefore, the method according to the invention was applied for examining the efficacy of donepezil therapy of patients with early-stage Alzheimer's disease. The diagnosis of Alzheimer's disease was made using the criteria laid down in DSM-5 (American Psychiatric Association, 2013). The average age of patients selected in the sample (n=10) was 75 years, their average education is 11.5 years, the sex ratio being 70% females to 30% males that reflects the general rate of occurrence of Alzheimer's disease. The cognitive tests were carried out twice during the study, at the onset of the therapy and following 3 months of taking donepezil. Of the standard psychometric tests, the MMSE, ADAS-Cog and clock drawing tests (all referred to in the introduction) were performed. The test results are summarized in FIG. 7. In the self-controlled study, performance in MMSE was not different after taking the acetylcholinesterase inhibitor for 3 months, and similarly, the effectiveness of the therapy could not be detected either with the ADAS-Cog or the clock drawing test.

In FIGS. 8A-8F, changes of the parameter values calculated with the method according to the invention are illustrated. The 3-month donepezil therapy significantly increased the duration of the speech samples 22 (FIG. 8A), and the speech rate (FIG. 8B), i.e. on average, the patients spoke more and more quickly during the test. As a result of the applied therapy, the number of silent pauses has decreased, and, although the number of filled pauses has slightly increased (FIG. 8C), the combined duration of silent pauses and filled pauses (FIG. 8D) and the ratio thereof to the total duration of the speech sample 22 (FIG. 8F) have both decreased. Therefore, the small increase in the number of filled pauses indicated in FIG. 8C was only the result of the increased speech duration. According to FIG. 8E, the number of any pauses during the total duration of the speech sample 22 (the combined number of silent and filled pauses) has significantly decreased as a result of the applied therapy.

In summary, it can be seen that, contrary to known methods, the method according to the invention is able to detect a significant difference that results from the 3-month donepezil therapy. Based on that, it can also be concluded that the sensitivity of the method according to the invention significantly surpasses the sensitivity of regularly applied test methods.

The computer program product according to the invention comprises instructions that, when the instructions are executed by a computer, cause the computer to carry out the steps of the method of to claim 1.

The computer-readable storage medium according to the invention comprises instructions that, when the instructions are executed by a computer, cause the computer to carry out the steps of the method of to claim 1.

The mode of industrial applicability of the invention follows from the essential features of the technical solution according to the foregoing description. It is apparent from the above description that the invention has fulfilled the objectives set before it in an exceedingly advantageous manner compared to the state of the art. The invention is, of course, not limited to the preferred embodiments described in details above, but further variants, modifications and developments are possible within the scope of protection determined by the claims.

The invention claimed is:

1. A method for automatic detection of neurocognitive impairment, comprising,
   generating, in a segmentation and labelling step, a labelled segment series from a speech sample using a speech recognition unit; and
   generating from the labelled segment series, in an acoustic parameter calculation step, acoustic parameters characterizing the speech sample;
characterised by
   determining, in a probability analysis step, in a particular temporal division of the speech sample, respective probability values corresponding to silent pauses, filled pauses and any types of pauses for respective temporal intervals thereof;
   calculating, in an additional parameter calculating step, a histogram by generating an additional histogram data set from the determined probability values by dividing a probability domain into subdomains and aggregating durations of the temporal intervals corresponding to the probability values falling into the respective subdomains; and
   generating, in an evaluation step, decision information by feeding the acoustic parameters and the additional histogram data set into an evaluation unit, the evaluation unit using a machine learning algorithm.

2. The method according to claim 1, characterised by applying phoneme labels, silent pause labels and filled pause labels in the segmentation and labelling step.

3. The method according to claim 2, characterised by applying separate respective phoneme labels for each phoneme in the segmentation and labelling step.

4. The method according to claim 1, characterised by dividing, for the probability analysis step, the speech sample into temporal intervals of identical lengths.

5. The method according to claim 4, characterised by dividing the speech sample into overlapping temporal intervals.

6. The method according to claim 5, characterised by applying temporal intervals having a length of 10-50 ms and overlapping with each other to an extent of 20-50%.

7. The method according to claim 4, characterised by determining, in the segmentation and labelling step, elements and labels of the labelled segment series based on a highest probability value occurring in the corresponding temporal intervals.

8. The method according to claim 1, characterised by dividing, in the additional parameter calculating step, the entire probability domain into subdomains of equal size.

9. The method according to claim 1, characterised by calculating, in the additional parameter calculating step, a cumulative histogram, by generating the elements of the additional histogram data set
from intervals having a probability that is higher than a lower limit of the respective probability subdomain, or
from intervals having a probability that is lower than an upper limit of the respective probability subdomain.

10. The method according to claim 1, characterised by applying, in the evaluation step, a two-sample statistical t-test for generating the decision information.

11. The method according to claim 1, characterised by determining a decision limit and an error limit of the decision limit as parts of the decision information.

12. The method according to claim 11, characterised by determining the decision limit using the machine learning algorithm of the evaluation unit by taking into account a bias of the machine learning algorithm.

13. The method according to claim 1, characterised by using, as an acoustic parameter, at least one parameter selected from the group consisting of a total duration of the speech sample, a speech rate, an articulation rate, a number of silent pauses, a number of filled pauses, a number of all pauses, a total length of silent pauses, a total length of filled pauses, a total length of all pauses, an average length of silent pauses, an average length of filled pauses, an average length of all pauses, a ratio of silent pauses in the speech sample, a ratio of filled pauses in the speech sample, a ratio of all pauses in the speech sample, a value obtained by dividing the number of silent pauses by the total duration of the speech sample, a value obtained by dividing the number of filled pauses by the total duration of the speech sample, and a value obtained by dividing the number of all pauses by the total duration of the speech sample.

14. The method according to claim 1, characterised by applying, in the evaluation step, an evaluation unit using a "Naive Bayes" (NB), linear "Support Vector Machine" (SVM) or "Random Forest"-type machine learning algorithm.

15. The method according to claim 1, characterised by providing the speech sample in a speech sample generation step.

16. Data processing system characterised by comprising, for performing the steps according to claim 1,
a speech recognition unit adapted for generating a labelled segment series from a speech sample,
a parameter extraction unit adapted for extracting acoustic parameters from the labelled segment series and connected to an output of the speech recognition unit,
an additional parameter extraction unit connected to the output of the speech recognition unit and adapted for generating an additional histogram data set, and
an evaluation unit connected to an output of the parameter extraction unit and an output of the additional parameter extraction unit, and adapted for performing the evaluation of the acoustic parameters and the additional histogram data set.

17. The data processing system according to claim 16, characterised by further comprising a sound recording unit connected to an input of the speech recognition unit, and/or a display unit connected to an output of the evaluation unit, and/or a database, the database being interconnected with the sound recording unit, with the speech recognition unit, with the parameter extraction unit, with the additional parameter extraction unit, with the evaluation unit and/or with the display unit.

18. A computer program product comprising a non-transitory computer-readable medium; and instructions stored on the non-transitory computer-readable medium which, when executed by a computer, cause the computer-to carry out the steps of the method of claim 1.

* * * * *